United States Patent [19]
Panitch

[11] Patent Number: 5,814,309
[45] Date of Patent: Sep. 29, 1998

[54] AEROSOL ANTIPERSPIRANT COMPOSITION

[75] Inventor: Maximo M. Panitch, Skokie, Ill.

[73] Assignee: Helene Curtis, Inc., Chicago, Ill.

[21] Appl. No.: 721,831

[22] Filed: Sep. 27, 1996

[51] Int. Cl.$^6$ ............................... A61K 7/32; A61K 7/00; A61K 7/38

[52] U.S. Cl. ............................. 424/651; 424/66; 424/67; 424/68; 424/400; 424/401

[58] Field of Search .................................. 424/65, 66, 67, 424/68, 400, 401

[56] References Cited

U.S. PATENT DOCUMENTS

| | | |
|---|---|---|
| 3,420,932 | 1/1969 | Jones et al. . |
| 3,507,896 | 4/1970 | Jones et al. . |
| 4,152,416 | 5/1979 | Spitzer et al. . |
| 4,675,177 | 6/1987 | Geary . |
| 4,840,786 | 6/1989 | Johnson et al. . |
| 4,935,224 | 6/1990 | Russo et al. . |
| 5,281,409 | 1/1994 | Thayer et al. . |
| 5,368,842 | 11/1994 | Lederman et al. . |
| 5,578,563 | 11/1996 | Trinh et al. ............................. 510/513 |

FOREIGN PATENT DOCUMENTS

| | | |
|---|---|---|
| 928220 | 6/1973 | Canada . |
| 95/01775 | 1/1995 | WIPO . |
| 96/04884 | 2/1996 | WIPO . |

OTHER PUBLICATIONS

Handbook of Aerosol Technology, Second Edition, by Paul A Sanders, Ph.D., pp. 49–54 and pp. 165–171.

Solubility Effects in Product, Package, Penetration, and Preservation by Christopher D. Vaughan, Cosmetics & Toiletries vol. 103, Oct. 1988 pp. 47–69.

Using Solubility parameters in Cosmetics Formulation by C. D. Vaughan, J. Soc. Cosmet. Chem. vol. 37 (Sep./Oct. 1985) pp. 319–333.

Application for Patent Invention No. 74,12426, Republic of France, Publication No. 11.

Deodorants & Antiperspirants Documetary, Cosmetics & Toiletries, Dec. 1985, vol. 100.

*Primary Examiner*—Shelley A. Dodson
*Attorney, Agent, or Firm*—Matthew Boxer

[57] ABSTRACT

Transparent aerosol antiperspirant compositions comprising an active antiperspirant salt, a carrier capable of solubilizing the active antiperspirant salt and having an effective solubility parameter of about 11 to about 13, and a liquified hydrocarbon gas propellant are disclosed.

17 Claims, No Drawings

AEROSOL ANTIPERSPIRANT COMPOSITION

FIELD OF THE INVENTION

The present invention is directed to transparent aerosol antiperspirant compositions comprising an active antiperspirant salt; a carrier capable of solubilizing the active antiperspirant salt and having solubility parameter of about 11 to about 13; and a gas propellant comprising a liquified hydrocarbon or hydrocarbon blend. The aerosol antiperspirant compositions are transparent liquids; incorporate a relatively low amount of propellant; deliver the active antiperspirant salt to the skin in an esthetically appealing manner; and do not leave a visible white residue on skin or clothing. The present invention also is directed to methods of using the aerosol antiperspirant compositions.

BACKGROUND OF THE INVENTION

Active antiperspirant compounds have been delivered to the surface of skin from a variety of product forms well-known in the cosmetic art. These product forms include wax-based sticks, soap-based sticks, compressed powder sticks, roll-on suspensions, emulsions, gels, creams, pump sprays, and aerosols. Maximum antiperspirant efficacy is achieved when the active antiperspirant compound is deposited on, and adheres to, the skin, while inactive materials either are present in minimal quantities, or evaporate or are otherwise removed from the skin after application.

Antiperspirant compositions prepared as aerosols generally contain a propellant and a liquid concentrate containing all other active and inactive ingredients. The liquid concentrate typically has a milky or opaque appearance and is manufactured by complex methods. An ideal aerosol composition is phase stable for the life of the product, is effectively dispensed from a pressurized container without an objectionable or harmful cloud, does not leave a visible white residue on skin or clothing, and is esthetically appealing to the consumer. Aerosol antiperspirant compositions preferably possess the properties of nonoiliness and nontackiness, and should not impart a wet feeling to skin. Clarity, or transparency, of aerosol antiperspirant compositions also is a long-sought esthetic property. Another highly desirable, but hard to achieve, esthetic property is avoiding a visible residue, e.g., a white layer, that is left on the skin or clothing after application of the aerosol antiperspirant composition.

Aerosol antiperspirant compositions are used by spraying the composition onto an area of the body, such as the underarm, to apply a layer of the composition to the skin. The aerosol spray is produced by the rapid and violent boiling of the propellant upon release from a pressurized container through an atomizing valve into atmospheric pressure.

Aerosol antiperspirant compositions that do not contain a solubilized active antiperspirant salt are known in the art, but have serious disadvantages. For example, compositions containing insoluble antiperspirant salts often require shaking prior to each use in order to redisperse the insoluble antiperspirant salt that has separated from the composition. Compositions containing insoluble antiperspirant salts, and that do not require shaking prior to each use, typically include a relatively high percentage of suspending agents, like hydrophobic organoclays or hydrophilic colloidal silicas. The presence of an organoclay or a colloidal silica in an aerosol antiperspirant composition contributes significantly to whitening and staining of skin and clothing.

Another disadvantage of aerosol antiperspirant compositions that contain an insoluble antiperspirant salt is the problem of valve clogging during normal use of the product. Valve clogging occurs when spray rates are insufficient to ensure that solid particles can completely negotiate the valve path. Propellants, therefore, are commonly used at levels of at least about 50 weight percent of the composition to prevent deposition of solid materials within the valve passage. In products of this type, the total volatile organic content (VOC), to which the propellant is a contributor, can be an environmental concern. Generally, the use of a liquified, fully halogenated hydrocarbon gas propellant is avoided because of their ozone depleting potential and, consequently, their deleterious effect on the stratosphere.

A still further disadvantage of aerosol antiperspirant compositions that contain an insoluble antiperspirant salt is consumer discomfort caused by a dust cloud which can result when the product is dispensed. The dust cloud is a combination of the fine insoluble particles being dispersed from the valve orifice and an amount of antiperspirant product "bounce-off" arising from poor adhesion of the insoluble antiperspirant salt particles to the skin.

Investigators have sought ways to overcome these disadvantages in aerosol antiperspirant compositions, and have especially sought to produce transparent compositions. Transparent antiperspirant compositions are particularly favored by consumers because such aerosol products project the esthetic qualities of purity, safety, and an expectation of minimal whitening of skin and clothes.

Aerosol antiperspirant compositions containing a particulate active ingredient, suspending agents, fillers, and other solid particles dispersed in a liquid vehicle, formulated with a propellant, and packaged in a pressurized container are well known. These compositions are disclosed, for example, in U.S. Pat. No. 4,840,786; U.S. Pat. No. 4,675,177; U.S. Pat. No. 5,368,842; and in "Deodorant and Antiperspirant Formulary," Cosmetics & Toiletries, Dec. 12, 1985, vol. 100, pp. 65–75. Because these compositions contain particulate active antiperspirant compounds and suspending agents, the compositions, and other similar compositions, have a tendency to leave a white, staining residue on contacted skin or clothing.

U.S. Pat. No. 4,152,416; U.S. Pat. No. 4,935,224; and U.S. Pat. No. 5,281,409 disclose aerosol antiperspirant compositions capable of being dispensed with low mistiness and dustiness. Insoluble antiperspirant salts are present in conjunction with suspending aids, while propellant levels are greater than 50 percent, and generally greater than 70 percent. Each patent discloses use of a polymeric additive to reduce dustiness and mistiness by increasing adhesion of the particulate active antiperspirant to the skin. U.S. Pat. No. 4,152,416; U.S. Pat. No. 4,935,224; and U.S. Pat. No. 5,281,409 are not directed to a transparent antiperspirant composition because the compositions disclosed therein contain an insoluble active antiperspirant salt and suspending aids.

WO 95/01775 discloses an aerosol antiperspirant composition comprising an active antiperspirant compound, a solvent capable of dissolving the active antiperspirant compound, and a propellant. Although the active antiperspirant composition initially is solubilized in the solvent, the compositions are designed such that upon addition of the propellant, at least a portion of the active antiperspirant compound is insolublized and precipitates. Thus, this composition also is not a transparent composition because of the presence of an insoluble, precipitated active antiperspirant compound.

Canadian Patent No. 928,220 discloses an aerosol antiperspirant composition comprising anhydrous ethyl alcohol, a solubilized active antiperspirant compound, and a liquified gas propellant mixture containing a hydrocarbon and a fully halogenated hydrocarbon. This composition requires fully halogenated hydrocarbon propellants, which have been banned in several countries because of their ability to deplete stratospheric ozone when released into the atmosphere.

French Patent Publication No. 2,267,086 discloses an aerosol antiperspirant composition containing a solubilized active antiperspirant compound, which is dissolved in an alcoholic, aqueous, or aqueous-alcoholic medium, together with nitrous oxide, alone or in combination with other compressed gas propellants and fully halogenated hydrocarbon liquified gas propellants. As discussed in *Handbook of Aerosol Technology*, 2nd ed., Robert E. Krieger Publishing Co., Malabar, Fla. (1979), pp. 49–55, incorporated herein by reference, a disadvantage associated with compressed gas propellants, such as nitrous oxide, nitrogen, and carbon dioxide, is that the internal pressure in the container generally is high, i.e., on the order of 70 to 90 psi (pounds per square inch), which limits the ability to package such a product in particular containers, for example, glass containers. Furthermore, the use of compressed gas propellants produces a wet spray, which adversely affects composition esthetics.

Another disadvantage of using compressed gas propellants, as set forth in *Handbook of Aerosol Technology*, pp. 49–55, is that the internal pressure of the container drops rapidly during periodic dispensing of the antiperspirant composition, with the undesirable result that the amount of composition applied to the skin varies. In addition, the spray characteristics of the composition change during discharge, with the possibility that the total contents of the container cannot be dispensed due to premature exhaustion of the compressed gas propellant. Yet another disadvantage of using a nitrous oxide compressed gas propellant is that mixtures of nitrous oxide and alcohols can be dangerous because of the oxidizing nature of nitrous oxide.

Therefore, investigators have continually sought to provide an aerosol antiperspirant composition which is transparent; is stable for the life of the product; is effectively and totally dispensed from a pressurized container without forming an objectionable or harmful cloud; does not leave a visible white residue on contacted skin or clothing; incorporates a relatively low amount of propellant; is not harmful to the environment; and is esthetically appealing to the consumer. The present invention is directed to providing such consumer-acceptable aerosol antiperspirant compositions.

SUMMARY OF THE INVENTION

The present invention is directed to transparent aerosol antiperspirant compositions, and to methods of using the compositions. More particularly, the present invention is directed to transparent aerosol antiperspirant compositions comprising an active antiperspirant salt; a carrier capable of solubilizing the active antiperspirant salt; and a liquified hydrocarbon or hydrocarbon blend as a gas propellant, such that the carrier has a solubility parameter in a range that prevents precipitation of the antiperspirant salt when the liquified gas propellant is added to the composition.

In particular, the transparent aerosol antiperspirant compositions comprise:
  (a) about 1% to about 25% by weight of an active antiperspirant salt;
  (b) about 30% to about 70% by weight of a carrier capable of solubilizing the active antiperspirant salt and having a solubility parameter value of about 11 to about 13, said carrier comprising, by weight of the composition:
    (i) about 15% to about 45% by weight of ethyl alcohol, and
    (ii) about 15% to about 55% by weight of an organic solvent having a solubility parameter value of about 8.5 to about 13.5, and preferably selected from the group consisting of a short chain ($C_1$–$C_6$) alcohol (excluding ethyl alcohol), a short chain ($C_1$–$C_6$) diol or polyol, a polyethylene glycol, a polypropylene glycol, a propylene glycol-ethylene glycol copolymer, propylene carbonate, ethylene carbonate, dimethoxymethane, and mixtures thereof; and
  (c) about 5% to about 32% by weight of a gas propellant comprising a liquified hydrocarbon or hydrocarbon blend.

The transparent aerosol antiperspirant compositions remain transparent over extended storage periods, do not whiten contacted skin or clothing, effectively deliver the active antiperspirant salt to the skin, and exhibit excellent esthetic and functional properties, including sensory properties, for consumer acceptance. The present aerosol antiperspirant compositions remain transparent for at least 12 months when stored at room temperature.

In a preferred embodiment, a transparent aerosol antiperspirant composition comprises:
  (a) about 5% to about 20% by weight of an active antiperspirant salt;
  (b) about 40% to about 65% by weight of a carrier capable of solubilizing the active antiperspirant salt and having an effective solubility parameter value of about 11 to about 13, said carrier comprising
    (i) about 20% to about 40% by weight of ethyl alcohol, and
    (ii) about 20% to about 45% by weight of an organic solvent having a solubility parameter value of from about 8.5 to about 13.5, and preferably selected from the group consisting of a short chain ($C_1$–$C_6$) alcohol (excluding ethyl alcohol), a short ($C_1$–$C_6$) chain diol or polyol, a polyethylene glycol, a polypropylene glycol, a propylene glycol-ethylene glycol copolymer, propylene carbonate, ethylene carbonate, dimethoxymethane, and mixtures thereof; and
  (c) about 8% to about 24% by weight of a gas propellant comprising a liquified hydrocarbon or hydrocarbon blend.

Advantages of the present invention include providing an aerosol antiperspirant composition which is transparent, is stable for the life of the product, is effectively dispensed from a pressurized container without generating an objectionable or harmful cloud, and does not leave a visible white residue on contacted skin or clothing. The present compositions incorporate a relatively low amount of propellant thereby having the benefit of introducing a low amount of volatile organic compounds to the atmosphere compared to conventional aerosol antiperspirant compositions, and do not incorporate environmentally harmful propellants, such as fully halogenated hydrocarbons. The compositions can be packaged in a variety of containers (including glass) which are recyclable and, therefore, less harmful to the environment, and are esthetically appealing to the consumer. The present invention is directed to providing consumer-acceptable aerosol antiperspirant compositions having these advantages. In addition, other advantages and novel features of the present invention will become apparent from the following detailed description of the preferred embodiments.

DETAILED DESCRIPTION OF THE PREFERRED EMBODIMENTS

A transparent aerosol antiperspirant composition of the present invention comprises an active antiperspirant salt, a carrier capable of solubilizing the active antiperspirant salt and having an effective solubility parameter of about 11 to about 13, and a gas propellant comprising a liquified hydrocarbon or hydrocarbon blend. The transparent aerosol antiperspirant composition is a liquid composition that is applied to the skin as a spray upon release from a pressurized container. After and during application, the propellant and other volatile components of the composition evaporate leaving the antiperspirant active salt and other nonvolatile composition ingredients in contact with the skin.

In accordance with an important feature of the present invention, the transparent aerosol antiperspirant compositions effectively resist phase separation and precipitation of components over long time periods. Therefore, the transparent aerosol antiperspirant compositions are available for immediate application to the skin without the need to vigorously shake or agitate the composition in order to redisperse composition ingredients prior to use.

In particular, the transparent aerosol antiperspirant compositions comprise:

(a) about 1% to about 25% by weight of an active antiperspirant salt;

(b) about 30% to about 70% by weight of a carrier capable of solubilizing the active antiperspirant salt and having a solubility parameter value of about 11 to about 13, said carrier comprising, by weight of the composition:

(i) about 15% to about 45% by weight ethyl alcohol, and (ii) about 15% to about 55% by weight of an organic solvent having a solubility parameter value of about 8.5 to about 13.5, and preferably selected from the group consisting of a short chain ($C_1$–$C_6$) alcohol excluding ethyl alcohol, a short chain ($C_1$–$C_6$) diol or polyol, a polyethylene glycol, a polypropylene glycol, a propylene glycol-ethylene glycol copolymer, propylene carbonate, ethylene carbonate, dimethoxymethane, and mixtures thereof; and (c) about 5% to about 32% by weight of a gas propellant comprising a liquified hydrocarbon or hydrocarbon blend.

As used here and hereinafter, the term "transparent" is defined as at least 50% transmittance determined spectrophotometrically at 700 nm (nanometers). The transparency of the transparent aerosol antiperspirant compositions can be measured spectrophotometrically by measuring % transmittance at 700 nm (nanometers), using water as the standard for 100% transmittance.

The transparent aerosol antiperspirant compositions are stable to phase separation and precipitation of components, do not become hazy or milky during storage, and exhibit exceptional esthetic and functional properties. The transparent aerosol antiperspirant compositions are liquids, and are capable of delivering the active antiperspirant salt to the skin, and in preferred embodiments are essentially nonwhitening, i.e., do not leave a visually observable white residue on the skin or clothing.

I. The Active Antiperspirant Salt

The active antiperspirant salt of the present transparent aerosol antiperspirant composition includes any of the antiperspirant compounds known in the art, such as the astringent salts. The astringent salts include organic and inorganic salts of aluminum, zirconium, zinc, and mixtures thereof.

The anion of the astringent salt can be, for example, sulfate, chloride, chlorohydroxide, alum, formate, lactate, benzyl sulfonate or phenyl sulfonate. Exemplary classes of antiperspirant astringent salts include aluminum halides, aluminum hydroxyhalides, zirconyl oxyhalides, zirconyl hydroxyhalides, and mixtures thereof.

Exemplary aluminum salts include aluminum chloride and the aluminum hydroxyhalides having the general formula $Al_2(OH)_xQ_y.XH_2O$, wherein Q is chlorine, bromine or iodine; x is about 2 to about 5; x+y is about 6, wherein x and y are not necessarily integers; and X is about 1 to about 6. Exemplary zirconium compounds include zirconium oxy salts and zirconium hydroxy salts, also referred to as zirconyl salts and zirconyl hydroxy salts, and represented by the general empirical formula $ZrO(OH)_{2-nz}L_z$, wherein z varies from about 0.9 to about 2 and is not necessarily an integer, n is the valence of L, 2-nz is greater than or equal to 0, and L is selected from the group consisting of halides, nitrate, sulfamate, sulfate, and mixtures thereof.

The active antiperspirant salt is present in the transparent aerosol antiperspirant composition in an amount of about 1% to about 25%, preferably about 5% to about 20%, and most preferably about 8% to about 18%, by weight of the composition.

The active antiperspirant salts are soluble in polar solvents. Exemplary antiperspirant compounds, therefore, include, but are not limited to, aluminum bromohydrate, potassium alum, sodium aluminum chlorohydroxide lactate, aluminum sulfate, aluminum chlorohydrate, aluminum zirconium tetrachlorohydrate, an aluminum zirconium polychlorohydrate complexed with glycine, aluminum zirconium trichlorohydrate, aluminum zirconium octachlorohydrate, aluminum sesquichlorohydrate, aluminum sesquichlorohydrex PG, aluminum chlorohydrex PG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, and mixtures thereof. Numerous other useful antiperspirant compounds are listed in WO 91/19222 and in the *Cosmetic and Toiletries Fragrance Handbook*, The Cosmetic, Toiletry and Fragrance Association, Inc., Washington D.C., p. 56, 1989, hereinafter the *CTFA Handbook*, incorporated herein by reference.

Preferred active antiperspirant salts include the aluminum zirconium chlorides complexed with an amino acid, like glycine, and the aluminum chlorohydrates. Preferred aluminum zirconium chloride glycine complexes have an aluminum (Al) to zirconium (Zr) ratio of about 1.67 to about 12.5, and a total metal (Al+Zr) to chlorine ratio (metal to chlorine) of about 0.73 to about 1.93.

Particularly preferred active antiperspirant salts include the alcohol soluble complexes of aluminum salts described in U.S. Pat. No. 3,420,932 and U.S. Pat. No. 3,507,896, incorporated herein by reference. These alcohol soluble complexes of aluminum salts are sold under the tradename REHYDROL II by Reheis Chemical Company, Inc., Berkeley Heights, N.J. REHYDROL II is a white, free-flowing, hygroscopic powder freely soluble in water and anhydrous ethyl alcohol at room temperature up to concentrations of about 50%.

II. The Carrier

The present transparent aerosol antiperspirant compositions also comprise a carrier capable of solubilizing the active antiperspirant salt, and having a solubility parameter value of about 11 to about 13. The carrier is present in an amount of about 30% to about 70%, preferably about 40% to about 65%, and most preferably about 50% to about 60%, by weight of the composition.

The carrier comprises about 15% to about 45% ethyl alcohol, by weight of the composition, combined with about 15% to about 55%, by weight of the composition, of an organic solvent having a solubility parameter value of about 8.5 to about 13.5. Preferably, the organic solvent is selected from the group consisting of short chain ($C_1$–$C_6$) alcohols excluding ethyl alcohol, short chain ($C_1$–$C_6$) diols and polyols, polyethylene glycols of weight average molecular weight ($M_w$) 600 or less, polypropylene glycols of $M_w$ 600 or less, propylene glycol-ethylene glycol copolymers of $M_w$ 600 or less, propylene carbonate, ethylene carbonate, dimethoxymethane, and mixtures thereof.

The use of solubility parameters in formulating cosmetic compositions is known. See, for example, C. D. Vaughan, "Using Solubility Parameters in Cosmetics Formulation," *Journal of the Society of Cosmetic Chemists*, Sept./Oct. 1985, Vol. 36, pp. 319–333; C. D. Vaughan, "Solubility Effects in Product, Package, Penetration, and Preservation," *Cosmetics & Toiletries*, Oct. 1988, Vol. 103, pp. 47–69; and *Handbook of Aerosol Technology*, 2nd ed., Robert E. Krieger Publishing Co., Malabar, Fla. (1979), pp. 165–171.

As discussed in *Handbook of Aerosol Technology*, 2nd ed., when designing homogeneous, i.e., transparent, compositions, solubility parameters can be a useful tool. For example, when an aerosol propellant is added to a liquid antiperspirant concentrate, which typically contains an active antiperspirant salt dissolved in a solvent or solvent blend, the formation of a new solvent system results. The new solvent system contains the propellant plus the solvent or solvent blend. The new solvent system typically has different properties than the solvent or solvent blend, and is a better or a worse solvent for the active ingredient than the solvent of the original antiperspirant concentrate. An active antiperspirant salt typically is quite soluble in a polar solvent, like ethyl alcohol, and relatively insoluble in a mixture of a nonpolar hydrocarbon propellant and ethyl alcohol, which results in precipitation of the active antiperspirant salt from solution. In this case, it is necessary to either use a different propellant or change the solvent of the concentrate. Solubility parameters have been found to assist formulators in making such changes.

For example, as set forth in *Handbook of Aerosol Technology*, situations exist where a mixture of two solvents dissolve a particular compound, although neither solvent alone is capable of dissolving the compound. This phenomena is attributed to one of the solvents having too high a solubility parameter to dissolve the compound, whereas the second solvent has too low of a solubility parameter. However, the effective solubility parameter of the solvent mixture is sufficiently close to the solubility parameter of the compound such that the solvent mixture is capable of solubilizing the compound.

In accordance with the present invention, the ethyl alcohol portion of the carrier serves an important role by initially solubilizing the active antiperspirant salt. The remaining organic solvent portion of the carrier is selected from compounds having a solubility parameter value of about 8.5 to about 13.5, and is present in an amount which, in conjunction with the ethyl alcohol, provides a solubility parameter value for the carrier as a whole of about 11 to about 13. Surprisingly, it has been found that when such a carrier is present in the antiperspirant composition, the active antiperspirant salt remains solubilized after the addition of a liquified hydrocarbon gas propellant. The overall result is a homogeneous, transparent composition having desirable esthetics and that is consumer acceptable.

Examples of organic solvents useful in the carrier of the present invention include, but are not limited to, short chain ($C_1$–$C_6$) alcohols other than ethyl alcohol, such as n-propyl alcohol, isopropyl alcohol, and butanol. Nonlimiting examples of short chain ($C_1$–$C_6$) diols and polyols include glycerin, ethylene glycol, diethylene glycol, propylene glycol, sorbitol, dipropylene glycol, tripropylene glycol, and hexylene glycol. Preferred short chain diols and polyols are propylene glycol and dipropylene glycol.

Nonlimiting examples of polyethylene glycols are low molecular weight compounds sold under the tradename POLYGLYCOL by Dow Chemical Co., Midland, Mich., and under the tradename CARBOWAX by Union Carbide Corp., Tarrytown, N.Y., and designated in the *CTFA Handbook* as PEG-4, PEG-6, PEG-8, and PEG-12. A particularly preferred polyethylene glycol is PEG-4. Similarly, polypropylene glycols, or ethylene glycolpropylene glycol copolymers, having an $M_w$ of about 600 or less, can be used in the organic solvent portion of the carrier.

Another particularly preferred organic solvent is dimethoxymethane, having the structural formula $CH_3$—O—$CH_2$—O—$CH_3$ and sold under the tradename METHYLAL by Lambiotte et Cie S. A., Brussels, Belgium. Dimethoxymethane is a liquid having a boiling point of 108° F., and is freely miscible in ternary mixtures that contain at least 10% by weight ethyl alcohol. Other useful organic solvents are listed in C. D. Vaughan, *J. Soc. Cosmet. Chem.*, 36, (1985) at pages 329–331, and *Cosmetics and Toiletries*, 103, (1988) at pages 65–69, both incorporated herein by reference.

The proper choice of a relative amount of ethyl alcohol and organic solvent in the carrier provides a solubility parameter value that results in a transparent composition. The relative amounts of ethyl alcohol and organic solvent also effect the esthetics of the composition. For example, an aerosol antiperspirant composition having a carrier containing solely ethyl alcohol is perceived by consumers as a product that leaves a white residue on skin after application. This perception is attributed to the lack of nonvolatile ingredients in the composition that act as masking agents for the active antiperspirant salt as the salt precipitates on the skin when the ethyl alcohol evaporates.

Conversely, an aerosol antiperspirant composition having a carrier containing solely a short chain diol or polyol, such as propylene glycol, is perceived by consumers as a product that is slow to dry on skin, and that imparts a tacky feel. An additional disadvantage is the potential of inhibiting the antiperspirant salt because of a relatively high amount of nonvolatile ingredients in the composition.

III. The Propellant

The present transparent aerosol antiperspirant composition also contains a gas propellant comprising a liquified hydrocarbon or hydrocarbon blend, in an amount of about 5% to about 32%, preferably about 8% to about 24%, most preferably about 10% to about 20%, by weight of the composition.

Nonlimiting examples of hydrocarbon gas propellants include propane, n-butane, isobutane, n-pentane, and mixtures thereof. Dimethylether sold under the tradename DYMEL A by the DuPont Chemical Co., Wilmington, Del., in combination with a hydrocarbon, also can be used in the propellant. Partially halogenated hydrocarbons also can be used as the gas propellant. Preferably, isobutane, used singly or mixed with other hydrocarbons, particularly propane, is used as the propellant of the present transparent aerosol antiperspirant compositions. Most preferably, isobutane is used alone as the propellant.

IV. Optional Ingredients

In addition to the essential ingredients of the present invention, the antiperspirant compositions also can contain volatile and nonvolatile hydrocarbons, volatile and nonvolatile linear polydimethylsiloxanes, and cyclic polydimethylsiloxanes as emollients to impart lubricity. Examples of volatile and nonvolatile hydrocarbons are the PERMETHYL series of materials available from Presperse, Inc., Pottstown, Pa. Examples of volatile and nonvolatile linear polydimethylsiloxanes, i.e., dimethicones, are the DC200 and DC225 series of siloxanes available from Dow Corning, Inc., Midland, Mich., as well as the SF series of siloxanes available from General Electric Silicones, Waterford, N.Y. Examples of cyclic polydimethylsiloxanes, i.e., cyclomethicones, are DC244, DC245, DC344, and DC345 available from Dow Corning, Inc., as well as SF1173, SF1202, and SF1204, available from General Electric Silicones. Other useful silicones include dimethiconol, dimethicone copolyol, dimethicone copolyol ethers, and phenyl siloxanes.

The present antiperspirant compositions also can contain additional optional ingredients, such as emollient esters and fatty ($C_8$–$C_{22}$) alcohols. Non-limiting examples of emollient esters and fatty alcohols include isopropyl palmitate, isopropyl myristate, diisopropyl adipate, dioctyl adipate, the FINSOLV series of benzoate esters available from Finetex, Inc., Elmwood Park, N.J., and isostearyl alcohol. Other optional ingredients include perfumes, coloring agents, antioxidants, preservatives and ultraviolet absorbers to improve composition esthetics and consumer acceptance.

The present transparent aerosol antiperspirant compositions contain a relatively low amount, i.e., about 5% to about 32% by weight of the composition, of a liquified gas propellant. Within this weight range, the total volatile organic content of the composition is low compared to prior aerosol antiperspirants, which traditionally contain 50% by weight or more of a propellant. Accordingly, compositions of the present invention are less harmful to the environment. Furthermore, and surprisingly, an amount of propellant as low as about 10% by weight of the composition can be sufficient to completely dispense the composition from a pressurized container. Another surprising aspect of the present invention is that addition of the liquified hydrocarbon gas propellant to the antiperspirant salt dissolved in the carrier does not precipitate the solubilized active antiperspirant salt from the carrier. This feature is attributed to a judicious selection of a carrier having a solubility parameter value of about 11 to about 13, and of a hydrocarbon gas propellant that is compatible with the balance of the composition. The combination of these two features provides a transparent antiperspirant composition.

A transparent aerosol antiperspirant composition of the present invention is prepared by simply admixing composition ingredients at, or slightly above, room temperature. Contrary to prior methods of manufacturing aerosol antiperspirant compositions, a high shear mixing step, or a homogenization step, typically required to disperse suspending agents is obviated.

In particular, a transparent aerosol antiperspirant composition of the present invention is prepared by dissolving the active antiperspirant salt in the carrier, with moderate agitation at a temperature of about 20° C. to about 40° C. The remaining composition ingredients, including, for example, the optional volatile and nonvolatile emollients, dye, and fragrance, except the liquified gas propellant, then are added to the solution containing the antiperspirant and carrier, and the resulting solution is mixed until homogeneous. The homogeneous solution is sealed in a valved container, such as a glass container, and the liquified gas propellant then is injected into the container through the valve.

The following specific examples are illustrative of transparent aerosol antiperspirant compositions of the present invention. The present invention, however, is not limited to the specific examples set forth below. In the following examples, the amounts of the various ingredients are expressed as weight percent.

As demonstrated in the following examples, the present aerosol antiperspirant compositions are liquids, are phase-stable over the life of the product, do not become hazy or milky during storage, are easy to apply, and effectively deliver the active antiperspirant salt to the surface of the skin. Each of the following examples was prepared by the above-described method.

EXAMPLE 1

| Ingredient[1] | |
|---|---|
| Active Antiperspirant Salt[2] | 10 |
| Carrier[3] | 58 |
| Liquified Gas Propellant[4] | 32 |

[1]the amount of each ingredient is expressed as % by weight of the total composition;
[2]aluminum chlorohydrex PG, available commercially as REHYDROL II, from Reheis, Inc., Berkeley Heights, New Jersey, added as a 100% active material;
[3]a blend of 82.8% anhydrous ethyl alcohol, available commercially as SD Alcohol 40-2, from Quantum Chemical Corp., USI Division, Cincinnati, OH, added as a 92.7% active material by weight, and 17.2% dipropylene glycol; and
[4]a blend of 24% isobutane, 66% n-butane, and 10% propane available commercially from Diversified, Manhattan, IL, added as a 100% active material.

The composition of Example 1 demonstrates the basic features of the present invention. The antiperspirant composition of Example 1 was a transparent solution with a good tactile feel when sprayed onto the skin. The composition of Example 1 showed good stability in glass and metal containers at both reduced and elevated temperature storage for at least 2 months. The solubility parameter value of the carrier of Example 1 was 12.4. The composition of Example 1 did not leave a visible white residue on the skin either 30 minutes or 120 minutes after application to the skin.

The compositions of Examples 2 and 3 illustrate that incorporating a nonvolatile hydrocarbon into the composition does not adversely affect the transparency of antiperspirant compositions of the present invention.

EXAMPLE 2

| Ingredient[1] | |
|---|---|
| Active Antiperspirant Salt[2] | 9.3 |
| Carrier[3] | 54.0 |
| Isohexadecane[5] | 4.7 |
| Liquified Gas Propellant[4] | 32.0 |

[5]available commercially as PERMETHYL 101A from Presperse Inc., Pottstown, PA, added as a 100% active material.

The composition of Example 2 was a transparent solution with a good tactile feel when sprayed onto the skin. The composition of Example 2 showed good stability in glass and metal containers at both reduced and elevated temperature storage for at least 2 months. The solubility parameter value of the carrier of Example 2 was 12.4.

EXAMPLE 3

Ingredient[1]

| | |
|---|---|
| Active Antiperspirant Salt[2] | 10.0 |
| Carrier[6] | 50.2 |
| Isohexadecane[5] | 9.8 |
| Liquified Gas Propellant[4] | 30.0 |

[6]a combination of 80.1% SD Alcohol 40-2 and 19.9% dipropylene glycol.

The composition of Example 3 was a transparent solution with a good tactile feel when sprayed onto the skin. The composition of Example 3 showed good stability in glass and metal containers at both reduced and elevated temperature storage for at least 2 months. The solubility parameter value of the carrier of Example 3 was 12.4.

The composition of Example 4 illustrates that incorporating a nonvolatile silicone into the antiperspirant composition does not adversely affect the transparency of compositions of the present invention.

EXAMPLE 4

Ingredient[1]

| | |
|---|---|
| Active Antiperspirant Salt[2] | 10 |
| Carrier[7] | 50 |
| Phenyltrimethicone[8] | 10 |
| Liquified Gas Propellant[4] | 30 |

[7]a combination of 80% SD Alcohol 40-2 and 20% dipropylene glycol; and
[8]available commercially as DC556 from Dow Corning, Corp., Midland, MI, added as a 100% active material.

The composition of Example 4 was a transparent solution with a good tactile feel when sprayed onto the skin. The composition of Example 4 showed good stability in glass and metal containers at both reduced and elevated temperature storage for at least 2 months. The solubility parameter value of the carrier of Example 4 was 12.4.

The compositions of Examples 5 and 6 illustrate that incorporating a volatile silicone into the antiperspirant composition does not affect the transparency of compositions of the present invention.

EXAMPLE 5

Ingredient[1]

| | |
|---|---|
| Active Antiperspirant Salt[2] | 10 |
| Carrier[7] | 50 |
| Cyclomethicone[9] | 10 |
| Liquified Gas Propellant[4] | 30 |

[9]available commercially as DC245 from Dow Corning, Corp., Midland, MI, added as a 100% active material.

The composition of Example 5 was a transparent solution with a good tactile feel when sprayed onto the skin. The composition of Example 5 showed good stability in glass and metal containers at both reduced and elevated temperature storage for at least 2 months. The solubility parameter value of the carrier of Example 5 was 12.4.

EXAMPLE 6

| | |
|---|---|
| Ingredient[1] | |
| Active Antiperspirant Salt[2] | 10 |
| Carrier[10] | 50 |
| Cyclomethicone[9] | 10 |
| Liquified Gas Propellant[4] | 30 |

[10]a combination of 60% SD Alcohol 40-2 and 40% dipropylene glycol.

The composition of Example 6 was a transparent solution with a good tactile feel when sprayed onto the skin. The composition of Example 6 showed good stability in glass and metal containers at both reduced and elevated temperature storage for at least 2 months. The solubility parameter value of the carrier of Example 6 was 12.24.

The compositions of Examples 7 and 8 illustrate that incorporating a volatile silicone does not adversely affect the transparency of compositions of the present invention when the carrier includes propylene carbonate.

EXAMPLE 7

| | |
|---|---|
| Ingredient[1] | |
| Active Antiperspirant Salt[2] | 11.1 |
| Carrier[11] | 55.5 |
| Cyclomethicone[9] | 11.1 |
| Liquified Gas Propellant[4] | 22.3 |

[11]a combination of 40% SD Alcohol 40-2, 20% dipropylene glycol, and 40% propylene carbonate.

The composition of Example 7 was a transparent solution with a good tactile feel when sprayed onto the skin. The composition of Example 7 showed good stability in glass and metal containers at both reduced and elevated temperature storage for at least 2 months. The solubility parameter value of the carrier of Example 7 was 12.71.

EXAMPLE 8

| | |
|---|---|
| Ingredient[1] | |
| Active Antiperspirant Salt[2] | 10.0 |
| Carrier[12] | 55.0 |
| Cyclomethicone[9] | 5.0 |
| Liquified Gas Propellant[4] | 30.0 |

[12]a combination of 36.4% SD Alcohol 40-2, 18.2% dipropylene glycol, and 45.4% propylene carbonate.

The composition of Example 8 was a transparent solution with a good tactile feel when sprayed onto the skin. The composition of Example 8 showed good stability in glass and metal containers at both reduced and elevated temperature storage for at least 2 months. The solubility parameter value of the carrier of Example 8 was 12.75.

The composition of Example 9 illustrates that incorporating an ester emollient does not adversely affect the transparency of the antiperspirant compositions of the present invention.

EXAMPLE 9

Ingredient[1]

| | |
|---|---|
| Active Antiperspirant Salt[2] | 12.8 |
| Carrier[13] | 64.1 |

EXAMPLE 9

| Ingredient[1] | |
|---|---|
| Cyclomethicone[9] | 6.4 |
| C12–C15 Alkyl Benzoate[14] | 6.4 |
| Liquified Gas Propellant[4] | 10.3 |

[13]a combination of 40% SD Alcohol 40-2 and 60% propylene carbonate; and
[14]available commercially as FINSOLV TN from Finetex, Inc., Elmwood Park, NJ, added as a 100% active material.

The composition of Example 9 was a transparent solution with a good tactile feel when sprayed onto the skin. The composition of Example 9 showed good stability in glass and metal containers at both reduced and elevated temperature storage for at least 2 months. The solubility parameter value of the carrier of Example 9 was 13.0.

The composition of Example 10 illustrates that the amount of active antiperspirant salt can be substantially increased without adversely affecting the transparency of compositions of the present invention when the carrier includes dimethoxymethane.

EXAMPLE 10

| Ingredient[1] | |
|---|---|
| Active Antiperspirant Salt[2] | 18.2 |
| Carrier[15] | 54.7 |
| Cyclomethicone[9] | 18.2 |
| Liquified Gas Propellant[4] | 8.9 |

[15]a combination of 66.7% SD Alcohol 40-2 and 33.3% dimethoxymethane, available commercially as METHYLAL from Lambiotte et Cie S.A., Brussels, Belgium, added as a 100% active material.

The composition of Example 10 was a transparent solution with a good tactile feel when sprayed onto the skin. The composition of Example 10 showed good stability in glass and metal containers at both reduced and elevated temperature storage for at least 2 months. The solubility parameter value of the carrier of Example 10 was 11.2.

The composition of Example 11 illustrates that a volatile silicone, a nonvolatile silicone, and an emollient ester can be simultaneously incorporated into a present antiperspirant composition without adversely affecting the transparency of compositions.

EXAMPLE 11

| Ingredient[1] | |
|---|---|
| Active Antiperspirant Salt[2] | 12.5 |
| Carrier[16] | 54.7 |
| Cyclomethicone[9] | 7.4 |
| Phenyltrimethicone[8] | 6.6 |
| Isopropyl Palmitate | 8.6 |
| Liquified Gas Propellant[4] | 10.2 |

[16]a combination of 45.7% SD Alcohol 40-2, 15.7% dipropylene glycol, 22.9% propylene carbonate, and 15.7% METHYLAL.

The composition of Example 11 was a transparent solution with a good tactile feel when sprayed onto the skin. The composition of Example 11 showed good stability in glass and metal containers at both reduced and elevated temperature storage for at least 2 months. The solubility parameter value of the carrier of Example 11 was 11.98.

A transparent aerosol antiperspirant of the present invention demonstrates excellent sensory and functional properties. The compositions exhibited an excellent stability at both reduced and elevated temperature, as well as room temperature, and are free of a precipitate. The compositions eliminate the requirement of vigorous shaking to redistribute the active antiperspirant salt prior to use, and demonstrate reduced or no whitening of the skin and clothing after topical application.

It should be understood that the foregoing detailed description is given merely by way of illustration. Obviously, many modifications and variations of the invention as set forth above can be made without departing from the spirit and scope thereof and, therefore, only such limitations should be imposed as are indicated by the appended claims.

What is claimed is:

1. A transparent aerosol antiperspirant composition comprising:
   (a) about 1% to about 25% by weight of an active antiperspirant salt;
   (b) about 30% to about 70% by weight of a carrier capable of solubilizing the active antiperspirant salt and having a solubility parameter value of about 11 to about 13, and said carrier comprising:
      (i) about 15% to about 45% by weight of the composition of ethyl alcohol, and
      (ii) about 15% to about 55% by weight of the composition of an organic solvent having a solubility parameter value of about 8.5 to about 13.5; and
   (c) about 5% to about 32% by weight of a gas propellant comprising a liquified hydrocarbon or hydrocarbon blend.

2. The composition of claim 1 wherein the active antiperspirant salt is present in an amount of about 5% to about 20% by weight of the composition.

3. The composition of claim 1 wherein the antiperspirant salt is an astringent salt comprising aluminum, zirconium, zinc or a mixture thereof.

4. The composition of claim 1 wherein the active antiperspirant salt is selected from the group consisting of aluminum bromohydrate, potassium alum, sodium aluminum chlorohydroxy lactate, aluminum sulfate, aluminum chlorohydrate, aluminum zirconium tetrachlorohydrate, an aluminum zirconium polychlorohydrate complexed with glycine, aluminum zirconium trichlorohydrate, aluminum zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, and mixtures thereof.

5. The composition of claim 1 wherein the carrier is present in an amount of about 40% to about 65% by weight of the composition.

6. The composition of claim 1 wherein the organic solvent is selected from the group consisting of a short chain ($C_1$–$C_6$) alcohol excluding ethyl alcohol, a short chain ($C_1$–$C_6$) diol or polyol, a polyethylene glycol having a molecular weight of about 600 or less, a polypropylene glycol having a molecular weight of about 600 or less, a propylene glycolethylene glycol copolymer having a weight average molecular weight of about 600 or less, propylene carbonate, ethylene carbonate, dimethoxymethane, and mixtures thereof.

7. The composition of claim 1 wherein the organic solvent is selected from the group consisting of propylene glycol, dipropylene glycol, glycerin, dimethoxymethane, and mixtures thereof.

8. The composition of claim 1 further comprising a polydimethylsiloxane in an amount of about 1% to about 15% by weight of the composition.

9. The composition of claim 1 further comprising a hydrocarbon emollient in an amount of about 1% to about 15% by weight of the composition.

10. The composition of claim 1 further comprising an emollient ester or fatty alcohol in an amount of about 1% to about 15% by weight of the composition.

11. The composition of claim 8 further comprising an emollient ester or fatty alcohol in an amount of about 1% to about 15% by weight of the composition.

12. The composition of claim 1 wherein the gas propellant is present in an amount of about 8% to about 24% by weight of the composition.

13. The composition of claim 1 wherein the gas propellant is present in an amount of about 10% to about 20% by weight of the composition.

14. The composition of claim 1 wherein the gas propellant is selected from the group consisting of propane, n-butane, isobutane, n-pentane, a partially halogenated hydrocarbon, dimethyl ether, and mixtures thereof.

15. The composition of claim 6 wherein the gas propellant comprises isobutane, n-butane, propane, or mixtures thereof.

16. The composition of claim 11 wherein the gas propellant is isobutane, n-butane, propane, or mixtures thereof.

17. A method of treating or preventing malodors associated with human perspiration comprising topically applying an effective amount of a transparent aerosol antiperspirant composition to human skin, said composition comprising:

(a) about 1% to about 25% by weight of an active antiperspirant salt;

(b) about 30% to about 70% by weight of a carrier capable of solubilizing the active antiperspirant salt and having a solubility parameter value of about 11 to about 13, said carrier comprising:
  (i) about 15% to about 45% by weight of the composition of ethyl alcohol, and
  (ii) about 15% to about 55% by weight of the composition of an organic solvent having a solubility parameter value of about 8.5 to about 13.5; and (c) about 5% to about 30% by weight of a gas propellant comprising a liquified hydrocarbon or hydrocarbon blend.

* * * * *